US012315152B2

(12) United States Patent
Reicher et al.

(10) Patent No.: US 12,315,152 B2
(45) Date of Patent: May 27, 2025

(54) MACHINE LEARNING MODELS FOR AUTOMATED DIAGNOSIS OF DISEASE DATABASE ENTITIES

(71) Applicant: Imvaria Inc., Berkeley, CA (US)

(72) Inventors: Joshua Reicher, Albany, CA (US); Michael Muelly, Sunnyvale, CA (US)

(73) Assignee: Imvaria Inc., Berkeley, CA (US)

( * ) Notice: Subject to any disclaimer, the term of this patent is extended or adjusted under 35 U.S.C. 154(b) by 329 days.

(21) Appl. No.: 17/862,529

(22) Filed: Jul. 12, 2022

(65) Prior Publication Data

US 2024/0020824 A1 Jan. 18, 2024

(51) Int. Cl.
*G06T 7/00* (2017.01)
*A61B 6/00* (2006.01)
(Continued)

(52) U.S. Cl.
CPC ............ *G06T 7/0012* (2013.01); *A61B 6/032* (2013.01); *A61B 6/50* (2013.01); *A61B 6/5217* (2013.01);
(Continued)

(58) Field of Classification Search
CPC ......... G06T 7/0012; G06T 2207/10016; G06T 2207/10081; G06T 2207/20076; G06T 2207/20081; G06T 2207/20084; G06T 2207/30061; A61B 6/032; A61B 6/50; A61B 6/5217; G16H 30/40; G16H 50/20; G16H 50/70; G16H 50/60; G06N 3/0442; G06N 3/0464; G06N 3/09
See application file for complete search history.

(56) References Cited

U.S. PATENT DOCUMENTS 9,974,453 B2 5/2018 Fonte et al.
10,373,315 B2 8/2019 Mansi et al.
(Continued)

FOREIGN PATENT DOCUMENTS

CN 110909756 A * 3/2020
CN 113689928 A * 11/2021
(Continued)

*Primary Examiner* — Carol W Chan
(74) *Attorney, Agent, or Firm* — HARNESS, DICKEY & PIERCE, P.L.C.

(57) ABSTRACT

A computer system includes memory hardware configured to store a three-dimensional deep learning model, and a pathology outcome database including multiple computed tomography (CT) images each associated with a surgical pathology outcome value. Processor hardware is configured to execute instructions including, for each of the multiple CT images, obtaining the surgical pathology outcome value associated with the CT image, and assigning the CT image to a positive image training dataset or a negative image training dataset in response to the surgical pathology outcome value indicating whether the patient experienced a disease diagnosis corresponding to a target medical condition. The instructions include supplying the positive and negative training image datasets to the three-dimensional deep learning model to train the model to generate a target medical condition prediction output indicative of a likelihood that a patient will experience a future disease diagnosis corresponding to the target medical condition.

20 Claims, 10 Drawing Sheets

(51) Int. Cl.
*A61B 6/03* (2006.01)
*A61B 6/50* (2024.01)
*G16H 30/40* (2018.01)
*G16H 70/60* (2018.01)

(52) U.S. Cl.
CPC ............ *G16H 30/40* (2018.01); *G16H 70/60* (2018.01); *G06T 2207/10016* (2013.01); *G06T 2207/10081* (2013.01); *G06T 2207/20076* (2013.01); *G06T 2207/20081* (2013.01); *G06T 2207/20084* (2013.01); *G06T 2207/30061* (2013.01)

(56) References Cited

U.S. PATENT DOCUMENTS

| | | |
|---|---|---|
| 11,151,407 B2 | 10/2021 | Walach et al. |
| 2009/0310836 A1* | 12/2009 | Krishnan .............. G06T 7/0012 382/128 |
| 2016/0350919 A1 | 12/2016 | Steigauf et al. |
| 2022/0148714 A1* | 5/2022 | Aisaka .................. G16H 50/30 |

FOREIGN PATENT DOCUMENTS

| | | |
|---|---|---|
| EP | 3654343 A1 | 5/2020 |
| KR | 102179583 B1 * | 11/2020 |

* cited by examiner

MACHINE LEARNING MODELS FOR AUTOMATED DIAGNOSIS OF DISEASE DATABASE ENTITIES

FIELD

The present disclosure relates to machine learning models for automated diagnosis of disease database entities.

BACKGROUND

Interstitial lung disease (ILD) represents a wide spectrum of rare, architectural and inflammatory lung diseases, with over 200 different subtypes. Outcomes and treatments vary greatly depending on the specific ILD subtype. One ILD subtype of particular importance is idiopathic pulmonary fibrosis (IPF), an orphan disease and the most common and severe of the ILD classifications. Average life expectancy for a person having IPF is less than five years, and in many cases it is less than two years. Fortunately, new and emerging therapies have demonstrated substantial improvements in the management of these diseases. However, assignment of the correct therapy requires accurate diagnosis.

The overall prevalence of ILD ranges from 26.1 to 80.9 per 100,000 people (and may be even higher), while the prevalence of IPF ranges from 7.4 to 20.2 per 100,000 people. However, some ILDs have little overlap with IPF clinically (e.g., some cases of organizing pneumonia), and therefore are not part of the standard population undergoing work-up for possible IPF. Given the variability in practice standards and disease distribution, the actual prevalence of IPF within a population undergoing dedicated IPF work-up varies widely.

Definitive diagnosis in ILD is critical and in many cases requires surgical biopsy, which is associated with up to a 16% in-hospital mortality rate within 30 days. Prior to invasive procedures, non-invasive work-up steps may include assessment of pulmonary function tests (PFTs), clinical history, computed tomography (CT) imaging, etc. The American Thoracic Society (ATS) guidelines, which are harmonized with various international pulmonary guidelines, provide a framework for diagnosis and treatment. However, standard work-up suffers from large inter-clinician variability and suboptimal diagnostic performance.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computer system includes memory hardware configured to store a three-dimensional deep learning model, a pathology outcome database including multiple computed tomography (CT) images each associated with a surgical pathology outcome value, and computer-executable instructions, wherein each surgical pathology outcome value is indicative of whether a patient experienced a disease diagnosis corresponding to a target medical condition. The system includes processor hardware configured to execute the instructions. The instructions include, for each of the multiple CT images, obtaining the surgical pathology outcome value associated with the CT image, in response to the surgical pathology outcome value indicating the patient experienced the disease diagnosis corresponding to the target medical condition, assigning the CT image to a positive image training dataset, and in response to the surgical pathology outcome value indicating the patient did not experience the disease diagnosis corresponding to the target medical condition, assigning the CT image to a negative image training dataset. The instructions include supplying the positive training image dataset and the negative image training dataset to the three-dimensional deep learning model to train the model to generate a target medical condition prediction output, wherein the prediction output is indicative of a likelihood that a patient will experience a future disease diagnosis corresponding to the target medical condition.

In other features, the instructions further include, for each of the multiple CT images, obtaining at least one clinical factor parameter associated with the CT image, and assigning the CT image to the positive image training dataset or the negative image training dataset is based on both the surgical pathology outcome value and the at least one clinical factor parameter. In other features, the at least one clinical factor parameter includes a pulmonary function test output.

In other features, the surgical pathology outcome value includes at least one of a surgical biopsy result and a tissue assessment result. In other features, the instructions include optimizing the three-dimensional deep learning model to extract image pattern information from each of the multiple CT images. In other features, optimizing the three-dimensional deep learning model includes implementing a loss function which includes weighted focal loss. In other features, optimizing the three-dimensional deep learning model includes using a stochastic gradient descent algorithm with momentum.

In other features, the target medical condition includes interstitial lung disease (ILD). In other features, the target medical condition includes idiopathic pulmonary fibrosis (IPF). In other features, the instructions include calibrating the three-dimensional deep learning model via scaling methods to optimize probability correlates with result outputs of the three-dimensional deep learning model.

In other features, the three-dimensional deep learning model includes a convolutional neural network (CNN). In other features, the instructions include pre-training the three-dimensional deep learning model with a video-based three-dimensional general pre-training dataset. In other features, the positive training image dataset and the negative image training dataset each include one or more of a demographic data input, a lab result data input, a clinical questionnaire data input, and a multi-disciplinary clinical assessment data input.

In other features, the instructions further include determining an output threshold for the three-dimensional deep learning model. In other features, the positive training image dataset and the negative training image dataset do not include any CT images having human-assigned labels. In other features, the instructions do not include performing segmentation of the CT images prior to training the three-dimensional deep learning model. In other features, each of the multiple CT images includes a three-dimensional full stack of CT images including multiple layered slice images.

A method of automated diagnosis of disease database entities includes accessing multiple computed tomography (CT) images each associated with a surgical pathology outcome value, wherein each surgical pathology outcome value is indicative of whether a patient experienced a disease diagnosis corresponding to a target medical condition. For each of the multiple CT images, the method includes obtaining the surgical pathology outcome value associated with the CT image, in response to the surgical pathology outcome value indicating the patient experienced the disease diagnosis corresponding to the target medical condition, assigning the CT image to a positive image training dataset, and in response to the surgical pathology outcome value indicating the patient did not experience the disease diagnosis corresponding to the target medical condition, assigning the CT image to a negative image training dataset. The method includes supplying the positive training image dataset and the negative image training dataset to a machine learning model to train the model to generate a target medical condition prediction output, wherein the prediction output is indicative of a likelihood that a patient will experience a future disease diagnosis corresponding to the target medical condition.

In other features, the method includes, for each of the multiple CT images, obtaining at least one clinical factor parameter associated with the CT image, wherein assigning the CT image to the positive image training dataset or the negative image training dataset is based on both the surgical pathology outcome value and the at least one clinical factor parameter. In other features, the surgical pathology outcome value includes at least one of a surgical biopsy result and a tissue assessment result.

A method of automated diagnosis of disease database entities includes receiving a case processing request from at least one of a medical data storage system and an electronic case submission interface via an input application programming interface (API), wherein the case processing request includes at least one medical scan image and at least one medical data entry associated with a patient, extracting image data from the case processing request, the image data including at least one medical scan image of the patient, and extracting at least one of text data and lab data from the case processing request, the at least one of text data and lab data associated with a medical condition of the patient. The method includes selecting at least a portion of the medical scan image(s) according to specified selection criteria, normalizing the selected at least a portion of the medical scan image(s), converting the selected at least a portion of the medical scan image(s) to at least one mathematical representation for processing by a machine learning model implementation, supplying at least the at least one mathematical representation to a machine learning model to generate a target medical condition prediction output, wherein the target medical condition prediction output is indicative of a likelihood that a patient will experience a future disease diagnosis event corresponding to the target medical condition, and automatically transmit the target medical condition prediction output as an electronic transmission via an output API to a provider system associated with the patient.

In other features, the at least one medical scan image includes a computed tomography (CT) scan, and the target medical condition includes interstitial lung disease (ILD).

A method of automated processing of disease database entities includes receiving a case processing request via an application programming interface (API), the case processing request associated with a patient, extracting image data from the case processing request, the image data including at least one medical scan image of the patient, and extracting at least one of text data and lab data from the case processing request, the at least one of text data and lab data associated with a medical condition of the patient. The method includes selecting at least a portion of the medical scan image(s) according to specified selection criteria, wherein the specified selection criteria includes at least one of a slice thickness, an image reconstruction kernel, and a manufacturer associated with the at least one medical scan image, normalizing the selected at least a portion of the medical scan image(s), converting the selected at least a portion of the medical scan image(s) to at least one mathematical representation for processing by a machine learning model implementation, and automatically storing labeled case data in a case storage database, wherein the labeled case data includes the normalized selected portion(s) of the medical scan image(s).

In other features, the specified selection criteria includes all of the slice thickness, the image reconstruction kernel, and the manufacturer associated with the at least one medical scan image. In other features, selecting at least a portion of the medical scan image(s) includes verifying a specified threshold number of slices in a series based on at least one of specified anatomic size criteria, a specified numeric slice number range, and a specified series slice thickness.

In other features, selecting at least a portion of the medical scan image(s) includes verifying a three-dimensional volumetric contiguity and specified ordering of slices of the medical scan image(s). In other features, the case processing request includes a digital imaging and communications in medicine (DICOM) computed tomography (CT) image. In other features, the method includes parsing DICOM header text and numeric data to generate parsed case data, wherein the parsed case data includes a patient identifier, a demographic characteristic, and at least one of a slice thickness and a reconstruction kernel.

In other features, normalizing includes normalizing a series of the selected at least a portion of the medical scan image(s) into a three-dimensional volumetric format. In other features, the medical scan image(s) include a three-dimensional full stack of CT images including multiple layered slice images.

A computer system includes an input application programming interface (API) configured to receive a case processing request from at least one of a medical data storage system and an electronic case submission interface, wherein the case processing request includes at least one medical scan image and at least one medical data entry associated with a patient, and an ingestion pipeline module configured to automatically identify the at least one medical scan image and the at least one medical data entry from the received case processing request, and to perform at least one analysis threshold determination on the identified at least one medical scan image and at least one medical data entry. The system includes an analysis module configured to supply the identified at least one medical scan image to a three-dimensional deep learning model to generate a target medical condition prediction output, wherein the target medical condition prediction output is indicative of a likelihood that a patient will experience a future disease diagnosis event corresponding to the target medical condition, and an output API configured to automatically transmit the target medical condition prediction output via an electronic transmission to a provider system associated with the patient.

In other features, the input API is configured to receive the case processing request automatically via connection with a picture archive and communication system (PACS). In other features, the input API, the ingestion pipeline module, the analysis module and the output API are configured to communicate with one another to generate the target medical condition prediction output automatically without user intervention.

In other features, the input API, the ingestion pipeline module, the analysis module and the output API are configured to operate as a software-as-medical-device (SaMD) application to generate the target medical condition prediction output automatically without user intervention. In other features, the input API, the ingestion pipeline module, the analysis module and the output API do not include a visual user interface.

In other features, the output API is in communication with a medical software interface configured to transmit electronic health records. In other features, the at least one medical scan image includes a computed tomography (CT) scan image. In other features, the at least one medical scan image includes a three-dimensional full stack of CT images including multiple layered slice images. In other features, the target medical condition includes interstitial lung disease (ILD). In other features, the target medical condition includes idiopathic pulmonary fibrosis (IPF).

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

In various implementations, systems and methods are disclosed which may be used for automated diagnosis of clinical diseases, such as interstitial lung diseases. The systems may include, for example, a Receiver application programming interface (API) (e.g., for acquisition of imaging data, demographic data, laboratory data, clinical data, and so on in a cloud storage environment, etc.), an ingestion pipeline and analysis system module for data processing and analysis, and an output API for device output transmission In one example, the analysis system module may acquire specific cases of patients with interstitial lung diseases, and train a machine learning algorithm to recognize features associated with a final diagnosis as assigned in the context of a patient registry or a clinical trial. The system may reduce morbidity and mortality through improved noninvasive diagnosis. The Receiver API may enable external connections to, for example, medical data storage systems in standardized medical data formats, to enable receiving new clinical cases into the system. The ingestion pipeline module may automatically process and normalize case data for analysis. The Output API may transmit a final analysis report to another device, a user interface, a database, etc.

Automated Diagnosis System

Figure 1:
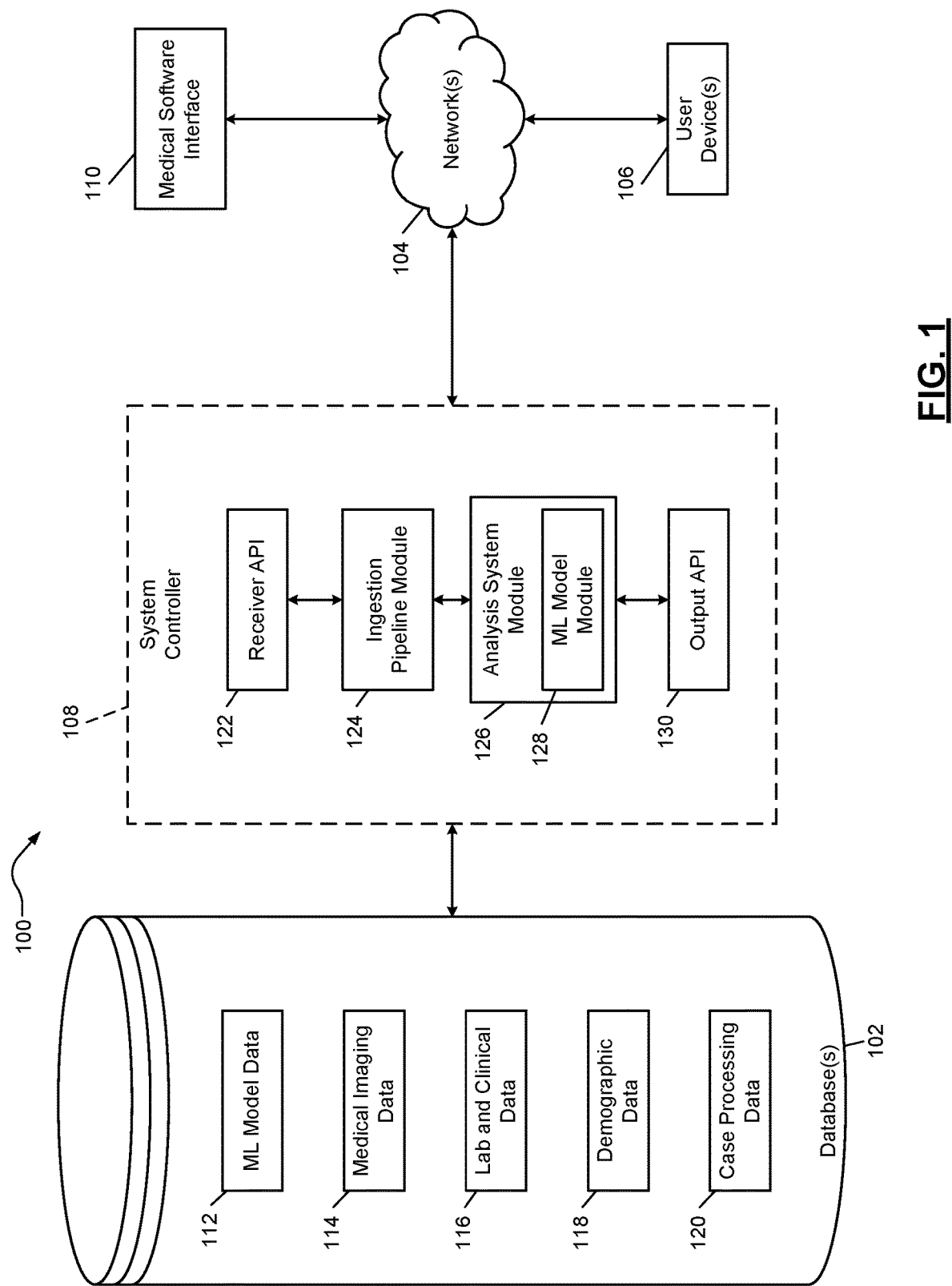
FIG. 1 is a functional block diagram of an example system for automated diagnosis of disease database entities.

FIG. 1 is a functional block diagram of an example system 100 for automated diagnosis of disease database entities, which includes a database 102. While the system 100 is generally described as being deployed in a computer network system, the database 102 and/or components of the system 100 may otherwise be deployed (for example, as a standalone computer setup). The system 100 may include a desktop computer, a laptop computer, a tablet, a smartphone, etc.

As shown in FIG. 1, the database 102 stores machine learning (ML) model data 112, medical imaging data 114, lab and clinical data 116, demographic data 118, and case processing data 120. In various implementations, the database 102 may store other types of data as well. The ML model data 112, the medical imaging data 114, the lab and clinical data 116, the demographic data 118, and the case processing data 120 may be located in different physical memories within the database 102, such as different random-access memory (RAM), read-only memory (ROM), a non-volatile hard disk or flash memory, etc. In some implementations, the ML model data 112, the medical imaging data 114, the lab and clinical data 116, the demographic data 118, and the case processing data 120 may be located in the same memory (such as in different address ranges of the same memory). In various implementations, the ML model data 112, the medical imaging data 114, the lab and clinical data 116, the demographic data 118, and the case processing data 120 may each be stored as structured or unstructured data in any suitable type of data store.

The ML model data 112 may include any suitable data for training one or more machine learning models (such as training a machine learning model to identify a disease diagnosis such as interstitial lung disease). For example, the ML model data 112 may include historical feature vector inputs that are used to train one or more machine learning models to generate a prediction output, such as a prediction of whether a patient has a specified disease diagnosis. The historical feature vector inputs may include the historical data structures which are specific to multiple historical database entities (such as multiple historical patients and patient case data).

In various implementations, users may run, train, etc. a model by accessing the system controller 108 via the user device 106. The user device 106 may include any suitable user device for displaying text and receiving input from a user, including a desktop computer, a laptop computer, a tablet, a smartphone, etc. In various implementations, the user device 106 may access the database 102 or the system controller 108 directly, or may access the database 102 or the system controller 108 through one or more networks 104. Example networks may include a wireless network, a local area network (LAN), the Internet, a cellular network, etc.

The system controller 108 may include one or more modules for automated diagnosis of disease database entities. For example, FIG. 1 illustrates the system controller 108 as including a receiver API 122, an ingestion pipeline module 124, an analysis system module 126, a ML model module 128, and an output API 130. The analysis system module 126 may include one or more machine learning model modules 128.

The receiver API 122 (or input API) may receive case data for automated disease diagnosis. For example, in various implementations the receiver API 122 may be accessed via any compliant medical data storage system (such as a picture archive and communication system, or PACS). A hospital or clinic system may access the receiver API 122 directly (e.g., via secure software integration), and submit the case electronically.

Alternatively, case data may be transmitted manually (e.g., by mail, etc.) to a device manufacturer (e.g., a manufacturer or operator of the automated diagnosis system), and the case data may be submitted by the manufacturer directly to the device/system through the receiver API 122. The receiver API 122 may pass the case data to the ingestion pipeline module 124.

The ingestion pipeline module 124 may accept the case data, select appropriate associated data for processing the case data, process the case data to prepare it for analysis (e.g., for supplying to a trained machine learning model), and store the processed data. For example, the ingestion pipeline module 124 may identify specific target data in the case received via the receiver API 122, verify that a data series is valid, complete quality checks, confirm data is adequate for analysis by a machine learning model, etc.

In various implementations, the ingestion pipeline module 124 may supply processed case data to the analysis system module 126 to generate an assessment of the case (e.g., a prediction of whether or not a patient associated with the case has a specified disease diagnosis). For example, the analysis system module 126 may include a three-dimensional (3D) deep learning model developed and trained using data from one or more facilities (such as the ML model module 128).

The analysis system module 126 may implement various phases, such as model pre-training, model training to a specified disease target, architecture optimization, threshold determination, validation, etc. In some implementations, an analysis algorithm of the analysis system module 126 may not perform any segmentation.

The output API 130 may transmit report data (e.g., a prediction of whether a patient has a specified disease diagnosis, a prediction of whether a patient has a target medical condition, case data identified as important in generating the prediction, etc.), to a clinician for review. For example, the output API 130 may be integrated into a hospital or clinic notification software system (e.g., electronic health records) for electronic transmission.

Alternatively, or in addition, the output API 130 may be used by, for example an automated disease diagnosis system/device manufacturer or operator to transmit an assessment report in human-readable format directly (e.g., via fax). The clinician may then incorporate the assessment report as part of diagnostic decision-making. In various implementations, the receiver API 122 and the output API 130 may communicate with a medical software interface 110 to obtain patient case data for analysis, transmit assessment reports for review or storage, etc. For example, the medical software interface 110 may include a medical data storage system, an electronic case submission interface, etc.

Referring back to the database 102, the medical imaging data 114 may include any suitable images associated with patients, such as computed tomography (CT) scans, magnetic resonance imaging (MIll) scans, camera image captures, etc. The lab and clinical data 116 may include any suitable lab data or clinical data associated with patients, such as lab test results, assessments by physicians, patient measurements, clinical reports or notes on patient conditions, medical history, prescription drug fill history, electronic health records, etc.

The demographic data 118 may include any suitable demographic data associated with patients, such as a patient name, address, date of birth, age, race, ethnicity, phone number, employment status, medical and prescription drug insurance coverage, social media information, and so on. The case processing data 120 may include any suitable data for processing cases to generate assessments, such as case data ingestion rules, specified machine learning algorithms to use, specified disease diagnosis targets, etc. In various implementations, more or less (or other) data may be stored in the database 102. The database 102 may be considered as a record database where various data is stored in multiple data structures.

Figure 2:
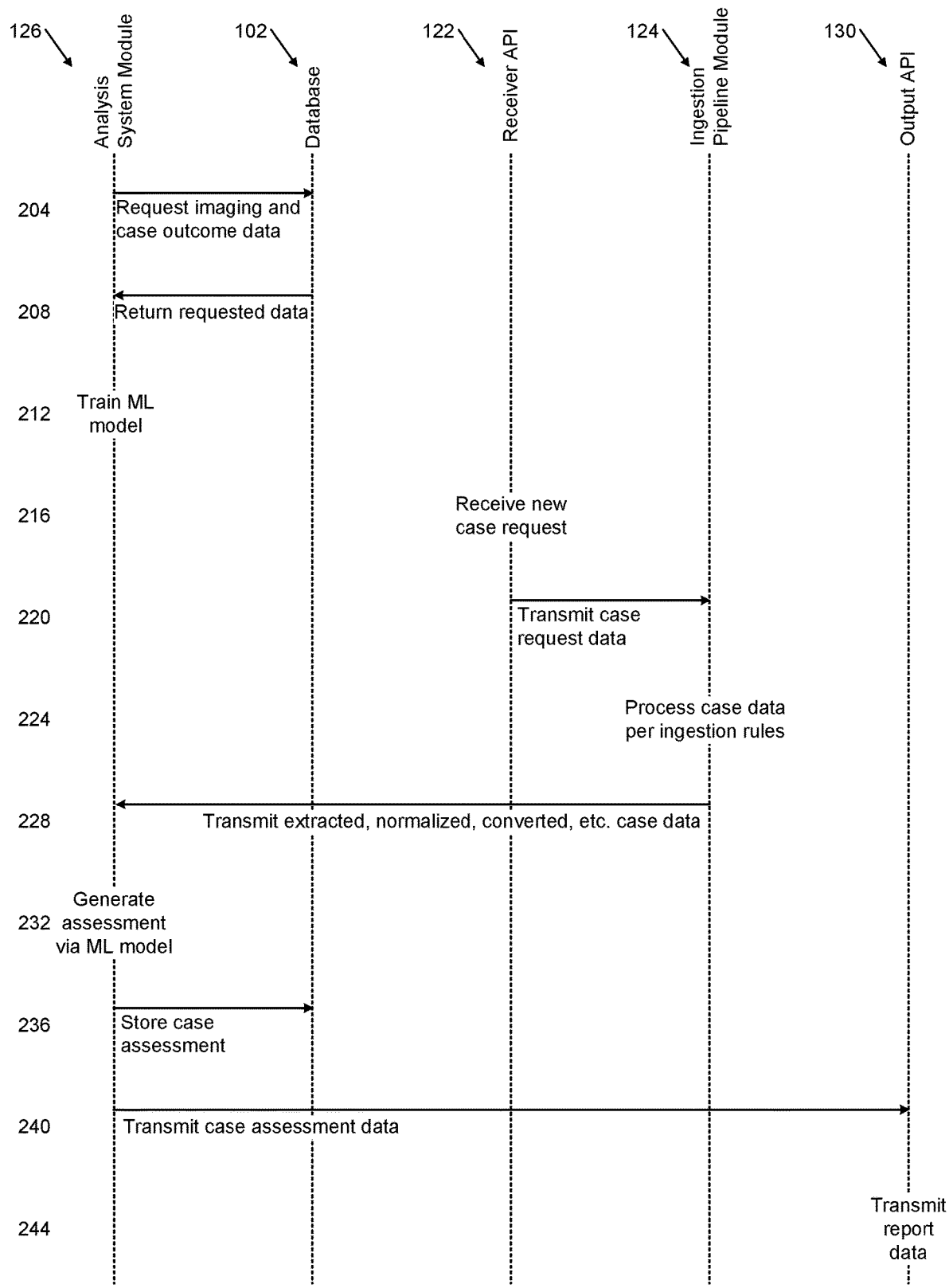
FIG. 2 is a message sequence chart illustrating example interactions between components of the system of FIG. 1.

FIG. 2 is a message sequence chart illustrating example interactions between the database 102, the analysis system module 126, the receiver API 122, the ingestion pipeline module 124, and the output API 130. At line 204, the analysis system module 126 requests imaging and case outcome data from the database 102. For example, the analysis system module 126 may request historical patient imaging data and historical clinical diagnosis data associated with the patients.

At line 208, the database 102 returns the requested imaging and case outcome data. The analysis system module 126 trains a machine learning model using the imaging and case outcome data at line 212. For example, the analysis system module 126 may use historical imaging and other data (such as the ML model data 112) to train a model using actual case outcome clinical diagnoses, to determine whether the historical imaging and other data is associated with a positive disease diagnosis.

The receiver API 122 receives a new case request at line 216. For example, a physician may submit a new patient case for analysis using the receiver API 122 and the medical software interface 110. The receiver API then transmits the case request data to the ingestion pipeline module 124 at line 220.

At line 224, the ingestion pipeline module 124 processes the case data per one or more ingestion rules. For example, the ingestion pipeline module 124 may use the case processing data 120 to identify the relevant data in the received case data, normalize data, generate input vectors for supplying to the machine learning model module 128, etc. In various implementations, the ingestion pipeline module 124 may process medical imaging data 114, lab and clinical data 116, demographic data 118, etc. associated with a patient of the new case request received by the receiver API.

At line 228, the ingestion pipeline module 124 transmits the extracted, normalized, converted, etc. case data to the analysis system module 126. The analysis system module 126 then generates a case assessment using the machine learning model module 128, at line 232. For example, the machine learning model module 128 may use one or more trained machine learning models to process data formatted by the ingestion pipeline module 124, in order to generate a prediction of whether a patient associated with the new case request has a specified disease diagnosis (e.g., whether the patient may experience a future surgical event corresponding to the specified disease diagnosis, such as requiring surgery to address the specified disease diagnosis).

The analysis system module 126 stores the case assessment in the database 102, at line 236. For example, the analysis system module 126 may store a specified disease diagnosis prediction, supporting data that was identified as most important to generate the prediction, etc.

At line 240, the analysis system module 126 transmits the case assessment data to the output API 130. The output API 130 then transmits the report data at line 244. For example, the output API 130 may transmit a case assessment including the disease diagnosis prediction to a physician treating a patient associated with the case request, via the medical software interface 110.

Figure 3:
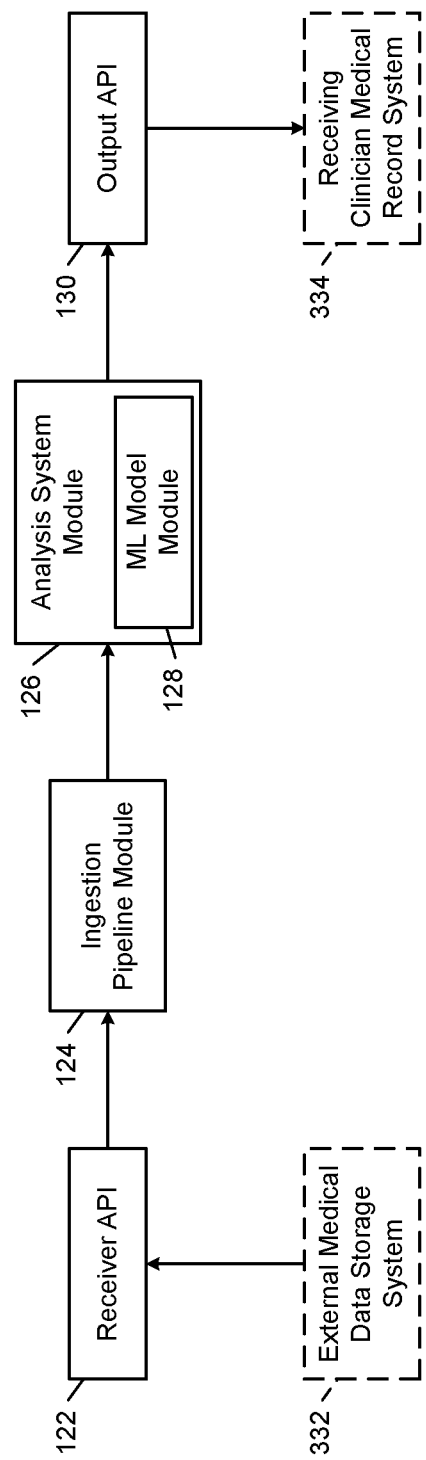
FIG. 3 is a diagram of an example processing pathway between modules of the system of FIG. 1.

FIG. 3 is a diagram of an example processing pathway between modules of the system of FIG. 1. In various implementations, a digital biomarker lab may support software-as-medical-device (SaMD) applications across multiple use cases. Each use case may follow a same or substantially similar algorithm for processing case data.

The system may be fully automated, end-to-end, where the sequence and subcomponents specify a novel device architecture that follows the same automated steps to process cases. While some analysis of medical imaging may involve a user interface component designed for an expert operator to manually manipulate and segment components of a medical image for partial processing by an analysis system, some example embodiments described herein (e.g., a digital biomarker lab) may not include a visual user interface because they instead complete all aspects of data processing and analysis without a human operator. This may be implemented by connecting to external medical software systems (such as via the medical software interface 110), in order to automatically receive new case request data and transmit case assessment results.

As shown in FIG. 3, a basic architecture of the system may include a representational state transfer (REST) API (e.g., the receiver API 122), which receives medical data into the system. For example, the receiver API 122 may use the medical software interface 110 to communicate with an external medical data storage system 332 to obtain new case data, including but not limited to medical imaging data, lab data, clinical data, demographic data, etc. In various implementations, the receiver API 122 may receive a digital imaging and communications in medicine (DICOM) CT scan folder.

The receiver API 122 provides data to the ingestion pipeline module 124, to automatically process the medical data for analysis. For example, the ingestion pipeline module 124 may automatically process a DICOM folder for analysis. The ingestion pipeline module 124 may then supply processed data to the analysis system module 126.

The analysis system module 126 may automatically analyze the medical data and generate an assessment result and/or report, such as a prediction of whether a patient associated with the received medical case data has a specified disease diagnosis. For example, the analysis system may automatically analyze metadata and images and generate a result and/or report to determine whether the analysis supports a diagnosis of a specified disease, such as idiopathic pulmonary fibrosis (IPF).

The analysis system module 126 transmits the case assessment report and/or result to the output API 130, which provides the report and/or result to a receiving clinician's medical record system 334. For example, the output API 130 may use the medical software interface 110 to supply the result and/or report back to the origin of the medical data case analysis request.

In various implementations, a clinical user (e.g., a clinician requesting the completion of the analysis) may use multiple methods to interrogate the system/device for analysis of the case. For example, the clinician may directly transmit the case data via hardcopy to the system/device manufacturer for internal processing, may directly transmit the case electronically (e.g., via DICOM integration), etc. Similarly, the case assessment result and/or report (e.g., disease diagnosis prediction) may be received via multiple methods at the selection of the clinical user, including but not limited to fax machine, secure e-mail, web portal, re-transmission to a standard health data system (e.g., electronic health record system or PACS), etc.

Example systems described herein may provide substantial improvements in non-invasive diagnosis, reducing the need for morbid and mortal invasive testing. In various implementations, example systems may use deep learning to predict diagnoses of diseases such as interstitial lung disease, provide a fully automated end-to-end process (e.g., input API, to automated medical data ingestion, to automated deep learning model inference, to output API) that does not require manual segmentation by a human operator prior to processing, may use orthogonal training endpoints (e.g., where the model is trained on CT images based on surgical pathology outcomes rather than on CT images labeled by expert image analyzers), may be used for diagnosis of diseases other than ILD, may use an artificial intelligence model to analyze a 3D CT image full stack (e.g., a three-dimensional full stack of CT images including multiple layered slice images), etc.

Automated Disease Diagnosis Process

Figure 4:
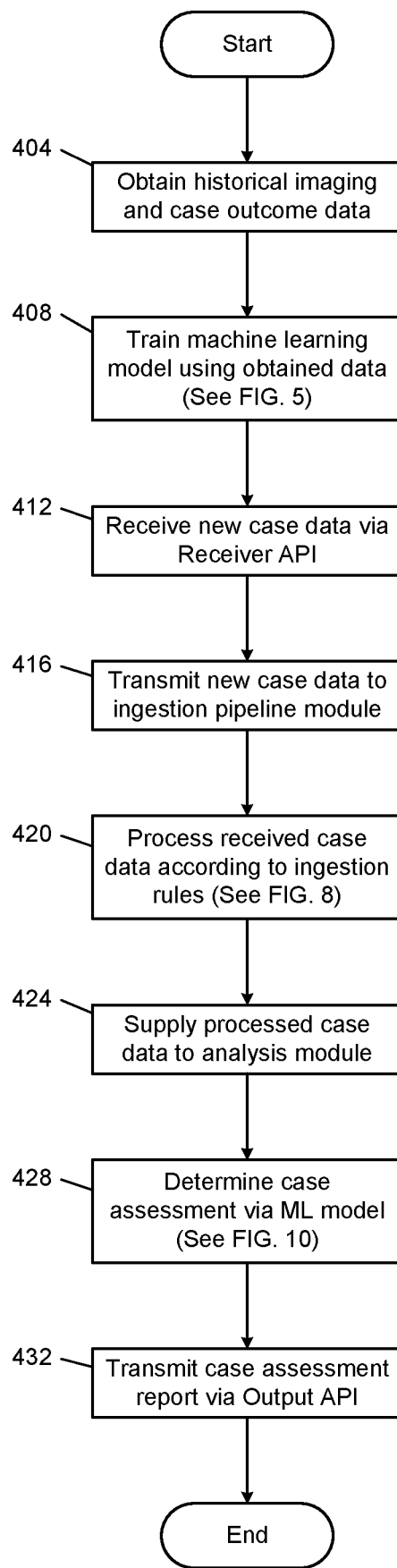
FIG. 4 is an example process for automated diagnosis of disease database entities.

FIG. 4 illustrates an example process for automated diagnosis of disease database entities, which may be performed by, for example, one or more modules of the system controller 108. Control begins at 404 by obtaining historical imaging and case outcome data. For example, control may obtain historical patient imaging data and historical surgical outcome diagnosis associate with the patients, such as from the ML model data 112.

At 408, control trains a machine learning model using the obtained data. For example, control may use the machine learning model module 128 to train a machine learning model to predict specified disease diagnoses. An example process for training a machine learning model is described in further detail below with reference to FIG. 5.

Control receives new case data via a receiver API, such as the receiver API 122, at 412. For example, the receiver API 122 may receive a new case request via the medical software interface 110, to determine whether a patient has a specified disease diagnosis. Control then transmits the received case data to the ingestion pipeline module, such as the ingestion pipeline module 124, at 416.

At 420, control processes the received case data according to ingestion rules. For example, the ingestion pipeline module 124 may use the case processing data 120 to format, extract, normalize, etc. the received new case data. An example algorithm for processing the new case data is described in further detail below with reference to FIG. 8.

Control supplies the processed case data to the analysis module, such as the analysis system module 126, at 424. Control then determines a case assessment using a machine learning model at 428. For example, the analysis system module 126 may use the machine learning model module 128 to predict whether a patient associated with the received case data has a specified disease diagnosis. An example process for determining a case assessment using a machine learning model is described in further detail below with reference to FIG. 10.

At 432, control transmits the case assessment report via the output API. For example, the output API 130 may transmit the prediction of whether the patient has a specified disease diagnosis via the medical software interface 110.

Figure 5:
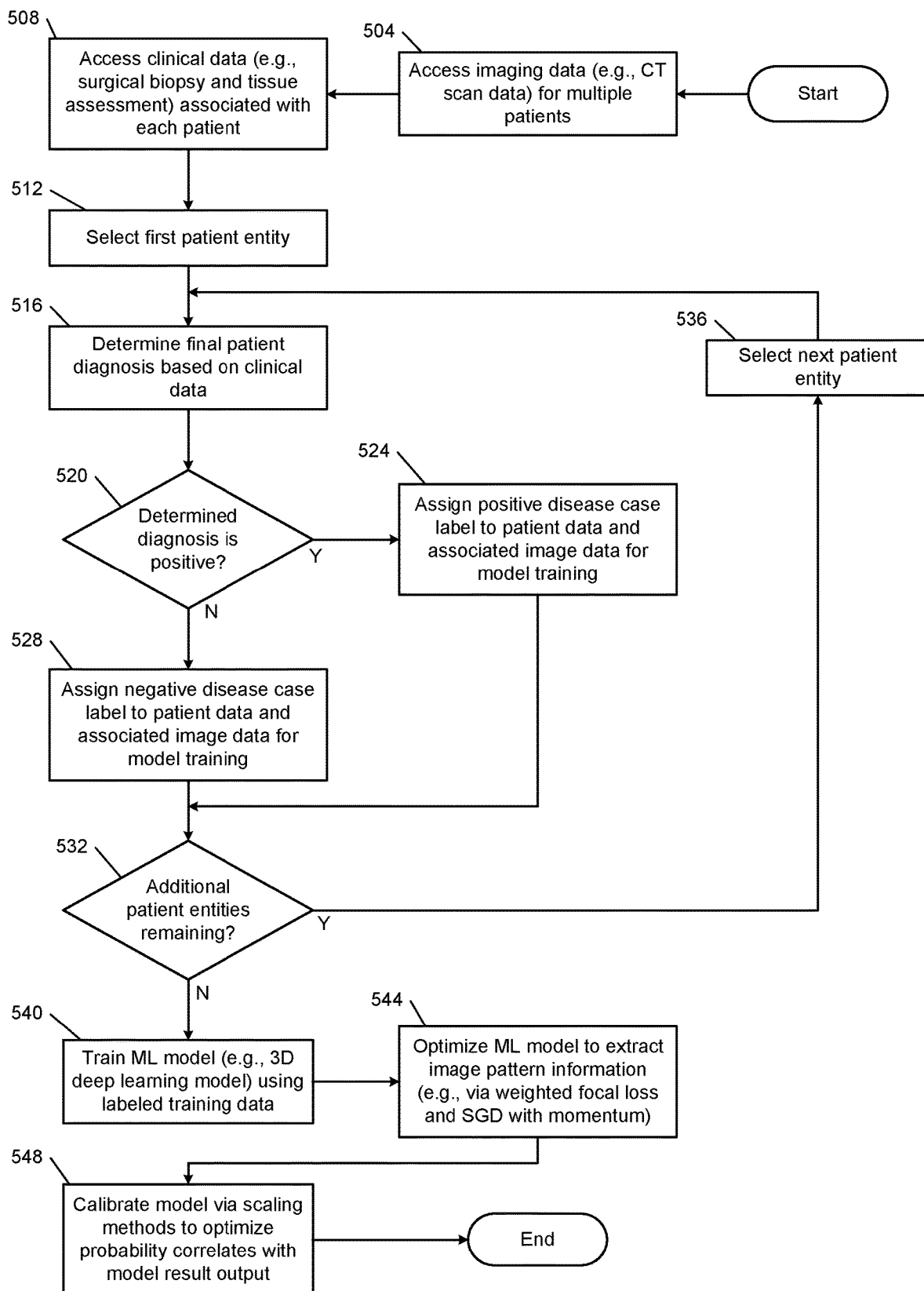
FIG. 5 is an example process for training a machine learning model to generate a likelihood prediction of a specified disease diagnosis.

FIG. 5 illustrates an example process for training a machine learning model to predict whether a patient has a specified disease diagnosis, which may be performed by, for example, the machine learning model module 128. Control begins at 504 by accessing image data (e.g., CT scan data) for multiple patients. For example, control may access historical patient images from the ML model data 112, the medical imaging data 114, etc.

At 508, control accesses clinical data associated with each patient, such as surgical biopsy and tissue assessment data. Control then selects a first patient entity (such as a first patient entry in a database), at 512. Control determines a final patient diagnosis based on clinical data. For example, control may analyze the surgical biopsy data, tissue assessment data, etc. to determine whether a patient had a prior surgical outcome diagnosis for a specified disease. Each patient entity, case data request, etc., may be considered as a disease database entity (e.g., a database may store multiple entries each associated with a patient and a positive or negative disease diagnosis or predicted disease diagnosis).

In various implementations, labels (such as a final diagnosis) for training data may be collected via registered clinical trials, patient registries, other sources such as an expert clinician determining the final diagnosis using data not directly assessed by the input data (e.g., determining an IPF diagnosis from pathology and clinical information and not just from the CT scan, whereas the algorithm may be allowed to look at the CT scan alone), situations where collected data is sufficient to provide a diagnostic or prognostic label based on standardized clinical calculations (e.g., "progressive ILD" may be defined by >10% lung function loss over a one year period so sequential lung function measurements may provide this information, and model training may then look back at the CT scan at time zero to see if the algorithm can predict such an outcome), etc. Training data labels may be assigned as a positive diagnosis, a negative diagnosis, other suitable classifications, etc.

In various implementations, labels for training data may be generated based on a combination of surgical pathology with other clinical factors. For example, a diagnosis of IPF may rely on CT images, pulmonary function tests, surgical pathology, other clinical factors, etc., to reach a conglomerate final diagnosis.

At 520, control determines whether the determined diagnosis is positive. If so, control proceeds to 524 to assign a positive disease case label to patient data and associated image data, or model training. If control determines at 520 that the determined diagnosis is negative, control proceeds to 528 to assign a negative disease case label to the patient data and associated image data, for model training. For example, control may determine whether the patient had a surgical outcome including the patient experiencing a disease diagnosis corresponding to a target medical condition, or if a surgical event such as a biopsy confirmed that the patient had a specified disease condition, etc.

Control then determines at 532 whether any additional patient entities remain for determination of positive or negative disease diagnosis outcomes. If additional patient entities remain that have not yet been labeled, control proceeds to 536 to select a next patient entity, and returns to 516 to determine a final patient diagnosis for the next selected patient entity based on clinical data associated with that selected patient entity.

Once control determines at 532 that no additional patient entities remain for positive or negative disease case labeling, control proceeds to 540 to train a machine learning model using the labeled training data. For example, control may use the labeled positive and negative case diagnosis outcomes to train a 3D deep learning model to predict a specified disease diagnosis based on medical imaging and patient clinical data.

At 544, control optimizes the machine learning model to extract image pattern information (e.g., via weighted focal loss and stochastic gradient descent (SGD) with momentum). Control then calibrates the model via scaling methods at 548, to optimize probability correlates with a model result output. For example, weighted focal loss may be used to reduce loss for relatively easier cases, and focus the network on training the relatively harder cases, such as by using a modulating factor multiplied with a cross-entropy loss.

In some example embodiments, temperature scaling may be used for calibration, although other embodiments may use any variety of suitable scaling methods. Scaling methods may be used to improve calibration of the prediction curve to more accurately reflect true underlying probabilities. For example, temperature scaling may be used as a post-processing method to address the tendency for neural networks to output overconfident probabilities, such as by dividing the logits (e.g., inputs to the softmax function) by a learned scalar parameter.

In various implementations, the analysis system algorithm(s) may be customized for specific use cases (such as diagnosing ILD), and may incorporate text information, numeric information, imaging information, etc. into the analysis (which may be automated). For example, a classifier may be used to assess and classify cases of interstitial lung disease (ILD) based on analysis of CT imaging. The algorithm(s) may include a 3D deep learning model, which may be developed and trained using data from multiple facilities. Example model development phases may include, but are not limited to, general model pre-training, model tuning to a specified disease target, model architecture optimization, model threshold determination, validation, etc.

For example, ingested case data may be supplied to a pre-trained model graph and processing code. The model may be pre-trained on hundreds to thousands of clinical cases, which may be selected for training based on ground truth diagnosis or outcomes (e.g., training data cases may be selected based on which patients had actual disease diagnosis based on prior surgical outcomes, etc.).

A model graph may be validated in multiple datasets before it is used for prediction. Any suitable models may be used for generating disease diagnosis predictions, such as a 3D deep learning model. In various implementations, an ideal output threshold for the model may be determined using any suitable techniques. An inference result may be generated by the model, and stored in a database.

In one example embodiment, a machine learning algorithm may be trained to evaluate ILD cases for evidence of idiopathic pulmonary fibrosis (IPF). The algorithm may be trained on, e.g., over one-thousand or more patients obtained from multiple locations. The training data may include multiple features, such as demographic data, lab result data, clinical questionnaire data, CT imaging data, pathology result data, multi-disciplinary clinical assessment data, etc.

The algorithm may be validated in any suitable number of patients, such as over one-thousand or more.

In various implementations, the algorithm architecture may use a video-based 3D general pre-training dataset. The algorithm architecture may be optimized to automatically extract image pattern information based on results of numerous research experiments. For example, a loss function may sue a weighted focal loss, an optimizer may use stochastic gradient descent (SGD) with momentum, etc. A final algorithm calibration may be achieved via, e.g., dedicated scaling methods to optimize probability correlates with algorithm result outputs.

A deep learning model may be trained using orthogonal outcome training. For example, the model may be trained to analyze non-invasively collected data (such as CT imaging), but with outcome labels assigned by surgical pathology and multi-disciplinary, multi-data-type driven labels, rather than image labels assigned by imaging experts. The model may be trained to predict diagnostic outcome, rather than to recognize pre-determined imaging features assigned by manual image reviewers.

In various implementations, the model may be trained via supervised learning. For example, supervised learning in image recognition, or computer vision, may include assigning image classification labels manually, and using the labels both for algorithm training and for algorithm evaluation (e.g., accuracy measurements). Typically, image classification labels themselves are assigned by a human. For example, one person, or a collection of people, may assign individually or as a group, image classifications of "dog" or "cat" to a set of images based on appearance. One challenge presented by this approach is that these labels can be wrong, based on human error. Another challenge is that not all cases will fall clearly into one category (such as an image containing both a dog and a cat).

Some example analysis algorithms described herein may be trained via a process that may be described as "super"-supervised learning. Given the challenges represented by supervised learning approaches, instead of assigning training labels for algorithm training based on human analysis of the images, some example embodiments may assign labels using alternative methods. For example, surgical biopsy and tissue assessment used to generate a final diagnosis in the clinical setting, may be used to assign labels to a case for training a machine learning model.

As an example, a machine learning model may be trained to analyze CT images. Rates of high variability may exist for human assessment of CT images alone, making pure human-assigned labels of imaging a problematic approach. In contrast, some example embodiments for training a classifier algorithm may assign labels to each training case via a combination of surgical pathology-obtained tissue assessment, full-context clinical assessment, patient demographics, lab results, clinical questionnaires, etc. In various implementations, no human-assigned labels of CT imaging may be included in the training process.

Machine Learning Model Examples

As described above, in various implementations, machine learning models may be used to predict specified disease diagnoses. Examples of various types of machine learning models that may be used for automated prediction of disease diagnoses are described below and illustrated in FIGS. 6 and 7, but example embodiments are not limited thereto.

Figure 6A:
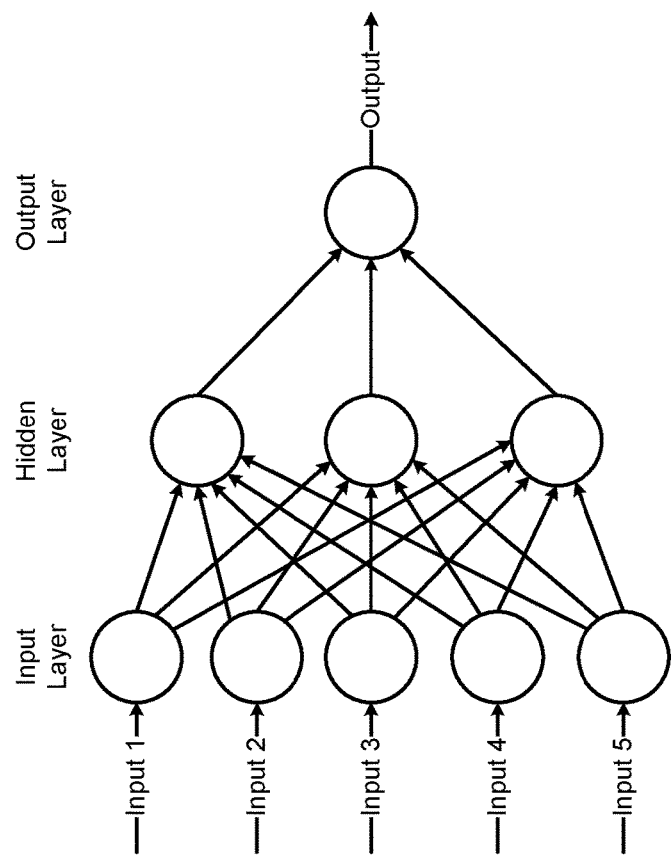
FIGS. 6A and 6B are graphical representations of example convolutional neural networks for automated prediction of a specified disease diagnosis.
Figure 6B:
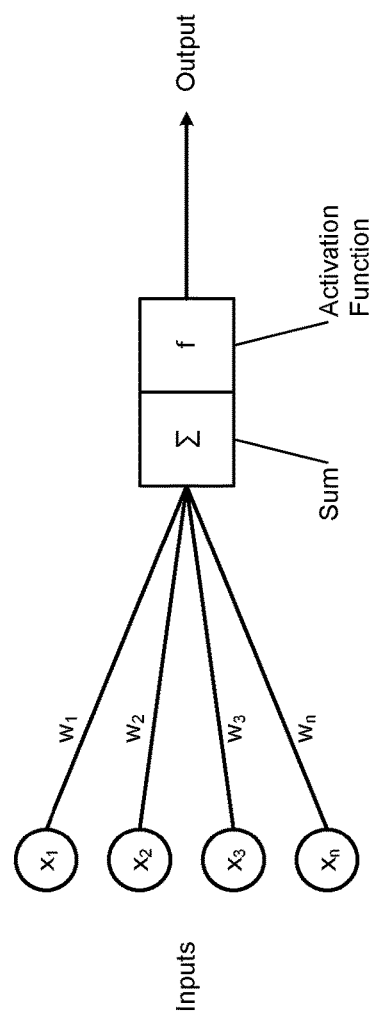

FIGS. 6A and 6B show an example of a convolutional neural network used to generate models such as those described above, using machine learning techniques. Machine learning is a method used to devise complex models and algorithms that lend themselves to prediction (for example, patient and provider matching predictions). The models generated using machine learning, such as those described above, can produce reliable, repeatable decisions and results, and uncover hidden insights through learning from historical relationships and trends in the data.

The purpose of using the convolutional neural-network-based model, and training the model using machine learning as described above, may be to directly predict dependent variables without casting relationships between the variables into mathematical form. The neural network model includes a large number of virtual neurons operating in parallel and arranged in layers. The first layer is the input layer and receives raw input data. Each successive layer modifies outputs from a preceding layer and sends them to a next layer. The last layer is the output layer and produces output of the system.

FIG. 6A shows a fully connected neural network, where each neuron in a given layer is connected to each neuron in a next layer. In the input layer, each input node is associated with a numerical value, which can be any real number. In each layer, each connection that departs from an input node has a weight associated with it, which can also be any real number (see FIG. 6B). In the input layer, the number of neurons equals number of features (columns) in a dataset. The output layer may have multiple continuous outputs.

The layers between the input and output layers are hidden layers. The number of hidden layers can be one or more (one hidden layer may be sufficient for most applications). A neural network with no hidden layers can represent linear separable functions or decisions. A neural network with one hidden layer can perform continuous mapping from one finite space to another. A neural network with two hidden layers can approximate any smooth mapping to any accuracy.

The number of neurons can be optimized. At the beginning of training, a network configuration is more likely to have excess nodes. Some of the nodes may be removed from the network during training that would not noticeably affect network performance. For example, nodes with weights approaching zero after training can be removed (this process is called pruning). The number of neurons can cause under-fitting (inability to adequately capture signals in dataset) or over-fitting (insufficient information to train all neurons; network performs well on training dataset but not on test dataset).

Various methods and criteria can be used to measure performance of a neural network model. For example, root mean squared error (RMSE) measures the average distance between observed values and model predictions. Coefficient of Determination ($R^2$) measures correlation (not accuracy) between observed and predicted outcomes. This method may not be reliable if the data has a large variance. Other performance measures include irreducible noise, model bias, and model variance. A high model bias for a model indicates that the model is not able to capture true relationship between predictors and the outcome. Model variance may indicate whether a model is stable (a slight perturbation in the data will significantly change the model fit).

As mentioned above, any suitable machine learning model architectures may be used to predict a specified disease diagnosis. For example, a convolutional neural network is a class of artificial neural network commonly applied to analyze visual images. In various implementations, a convolutional neural network may include an input layer, hidden layers and an output layer. In a feed-forward neural network, any middle layers may be referred to as hidden because their inputs and outputs are masked by the activation function and final convolution. In a convolutional neural network, the hidden layers include layers that perform convolutions. Typically, this includes a layer that performs a dot product of the convolution kernel with the layer's input matrix. For example, this product may be a Frobenius inner product, and its activation function may be ReLU. As the convolution kernel slides along the input matrix for the layer, the convolution operation generates a feature map, which in turn contributes to the input of the next layer. This may be followed by other layers such as pooling layers, fully connected layers, and normalization layers.

A long short-term memory (LSTM) neural network is another example machine learning model architecture, which may be used to generate models such as those described above. An example LSTM neural network may include an input layer, a hidden layer, and an output layer. The input layer includes multiple inputs, the hidden layer includes multiple neurons, and the output layer includes multiple outputs.

Each neuron of the hidden layer receives an input from the input layer and outputs a value to the corresponding output in the output layer. Each neuron may also receive an output of a previous neuron as an input. In this way the output of each neuron is fed forward to the next neuron in the hidden layer. The last output in the output layer outputs a probability associated with the inputs. Each layer may contain any number of elements.

In various implementations, each layer of the LSTM neural network must include the same number of elements as each of the other layers of the LSTM neural network. In some embodiments, a convolutional neural network may be implemented. Similar to LSTM neural networks, convolutional neural networks include an input layer, a hidden layer, and an output layer. However, in a convolutional neural network, the output layer includes one fewer output than the number of neurons in the hidden layer and each neuron is connected to each output. Additionally, each input in the input layer is connected to each neuron in the hidden layer.

In various implementations, each input node in the input layer may be associated with a numerical value, which can be any real number. In each layer, each connection that departs from an input node has a weight associated with it, which can also be any real number. In the input layer, the number of neurons equals number of features (columns) in a dataset. The output layer may have multiple continuous outputs.

As mentioned above, the layers between the input and output layers are hidden layers. The number of hidden layers can be one or more (one hidden layer may be sufficient for many applications). A neural network with no hidden layers can represent linear separable functions or decisions. A neural network with one hidden layer can perform continuous mapping from one finite space to another. A neural network with two hidden layers can approximate any smooth mapping to any accuracy.

Figure 7:
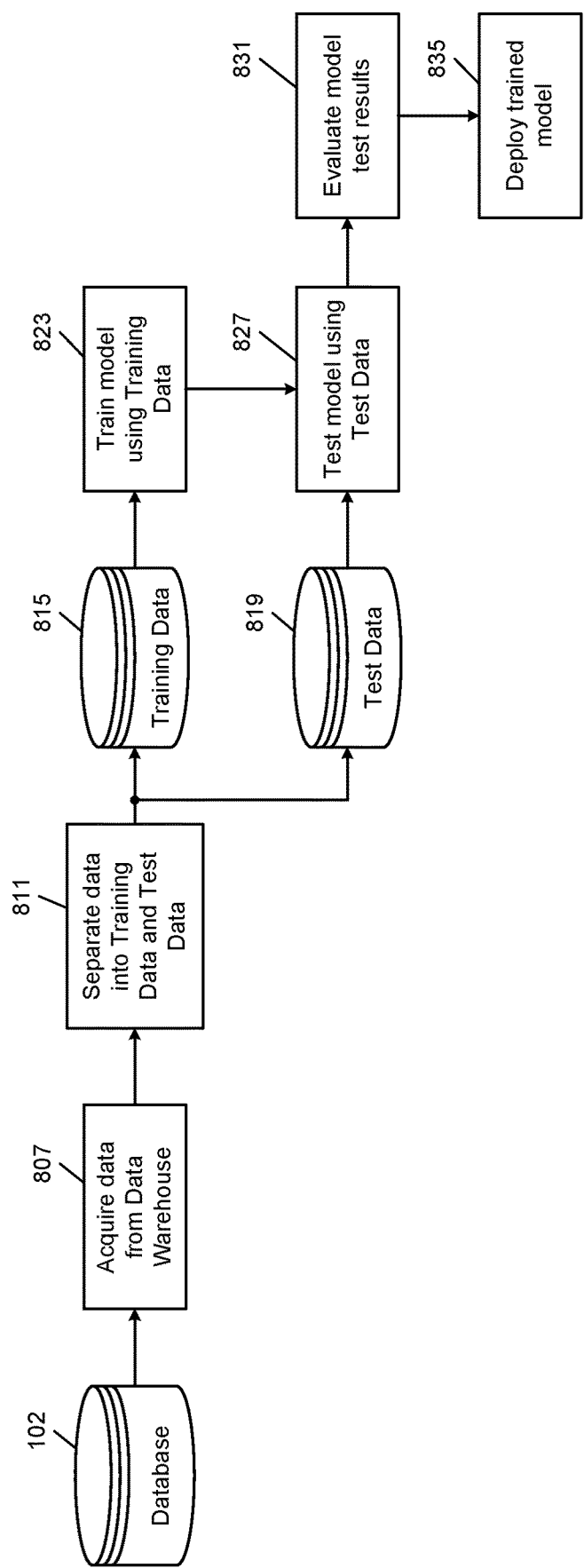
FIG. 7 is a flowchart illustrating an example process for training a machine learning model.

FIG. 7 illustrates an example process for generating a machine learning model. At 807, control obtains data from a database 102. The data may include any suitable data for developing machine learning models. At 811, control separates the data obtained from the database 802 into training data 815 and test data 819. The training data 815 is used to train the model at 823, and the test data 819 is used to test the model at 827. Typically, the set of training data 815 is selected to be larger than the set of test data 819, depending on the desired model development parameters. For example, the training data 815 may include about seventy percent of the data acquired from the database 802, about eighty percent of the data, about ninety percent, etc. The remaining thirty percent, twenty percent, or ten percent, is then used as the test data 819.

Separating a portion of the acquired data as test data 819 allows for testing of the trained model against actual output data, to facilitate more accurate training and development of the model at 823 and 827. The model may be trained at 823 using any suitable machine learning model techniques, including those described herein, such as random forest, generalized linear models, decision tree, and neural networks.

At 831, control evaluates the model test results. For example, the trained model may be tested at 827 using the test data 819, and the results of the output data from the tested model may be compared to actual outputs of the test data 819, to determine a level of accuracy. The model results may be evaluated using any suitable machine learning model analysis, such as the example techniques described further below.

After evaluating the model test results at 831, the model may be deployed at 835 if the model test results are satisfactory. Deploying the model may include using the model to make predictions for a large-scale input dataset with unknown outputs. If the evaluation of the model test results at 831 is unsatisfactory, the model may be developed further using different parameters, using different modeling techniques, using other model types, etc.

Data Ingestion and Analysis Process

Figure 8:
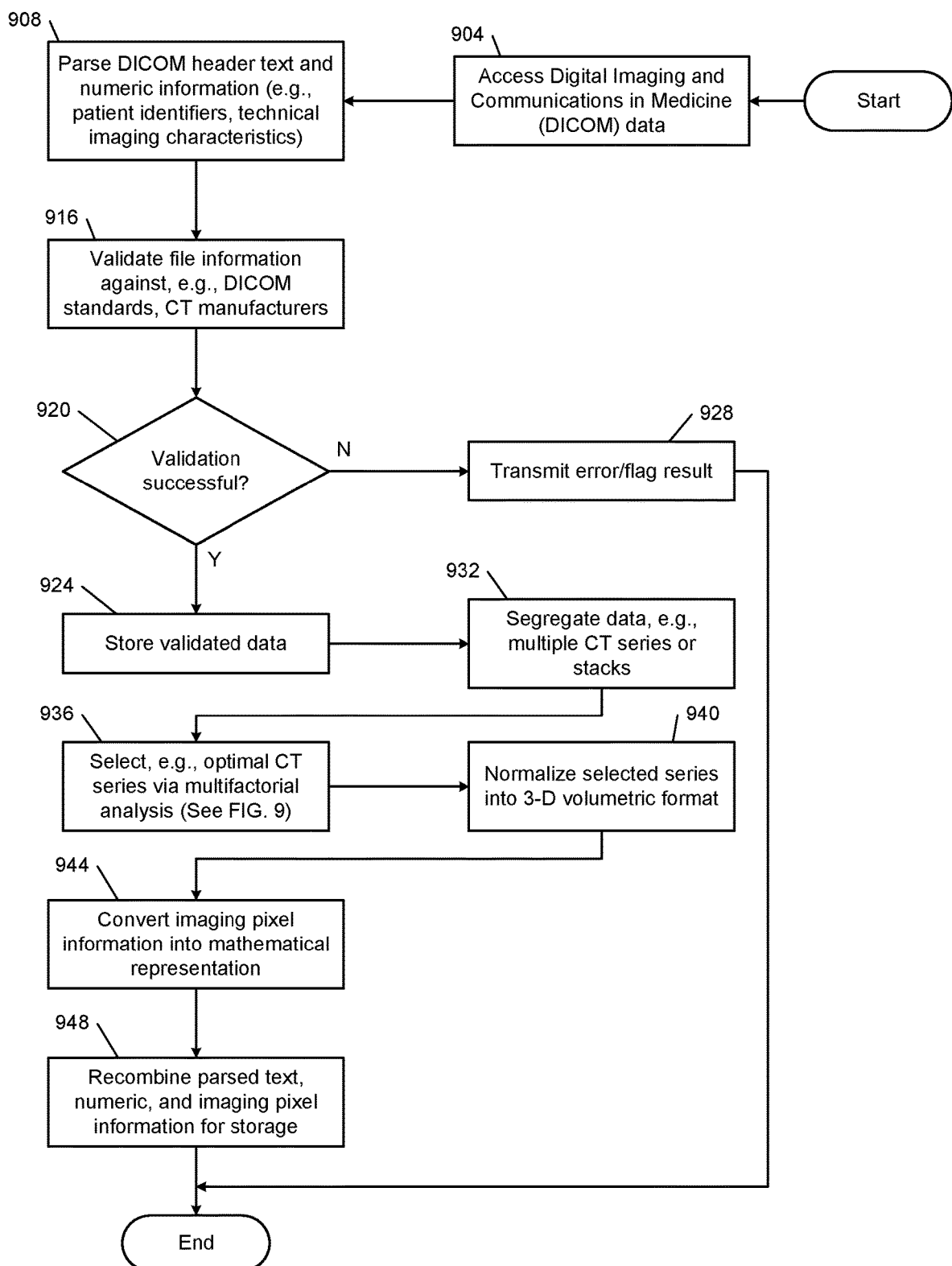
FIG. 8 is a flowchart illustrating an example method for processing a case request according to ingestion rules.

FIG. 8 illustrates an example method for processing new case request data according to ingestion rules, which may be performed by, for example, the ingestion pipeline module 124. At 904, control begins by accessing digital imaging and communications in medicine (DICOM) data.

At 908, control parses the DICOM header text and numeric information (e.g., patient identifiers, technical imaging characteristics, etc.). Control then validates the file information against, e.g., DICOM standards, CT manufacturers, etc., at 916. In various implementations, the ingestion pipeline module 124 may validate parsed information by checking slice thicknesses, series descriptions, CT manufacturers, image reconstruction kernels, etc., and prioritization may be used for optimal selection.

At 920, control determines whether a validation check was successful. If not, control transmits an error/flag result at 928 indicating that the validation was unsuccessful, and ends the process. If control determines at 920 that the validation was successful, control proceeds to store the validated data at 924 (such as in the database 102).

Control then proceeds to 932 to segregate the data, e.g., based on multiple CT series or stacks. At 936, control selects a CT series (e.g., an optimal CT series) via multifactorial checks. An example process for performing multifactorial checks is described further below with reference to FIG. 9.

At 940, control normalizes a selected series into a 3D volumetric format, and then converts imaging pixel information into a mathematical representation at 944. At 948, control recombines the parsed text, numeric and imaging pixel information for storage. For example, images may be center cropped, and may have a padded height and width to give standard dimensions and number of slices, pixel values may be set using desired or predetermined minimum and maximum value ranges, etc.

In various implementations, the ingestion pipeline module 124 may identify applicable data from an incoming case request, verify that the data is valid, complete quality checks, confirm the data is adequate for analysis, etc. The ingestion pipeline module 124 may execute a series of steps, which may be customized to a data type and refined to select optimal data elements needed for processing by the analysis system module 126 and the machine learning model module 128. For example, the ingestion pipeline module 124 may ingest case data, and separately extract imaging data and text/lab data for storage. Ingested case data may be automatically stored in the database 102 and labeled.

In some cases, a DICOM or other standard image format reader may be executed to read incoming case data. A sub-selection of images may be determined based on specified criteria, such as size, type, etc. Images may be parsed and normalized, in two dimensions, three dimensions, and beyond. Images may be converted to mathematical representations for processing by machine learning models.

In various implementations, a DICOM CT module may be used for chest imaging. The module may automatically extract, select and store optimal elements needed for chest CT imaging by the analysis system module 126, allowing for directed analysis of the lungs. For example, automated steps may include parsing of DICOM header text and numeric information including patient identifiers, demographic characteristics, and imaging characteristics (e.g., slice thickness, reconstruction kernel), etc. In various implementations, the ingestion pipeline module 124 may automatically identify one or more medical scan images, one or more medical data entries, etc., from a received case processing request.

Automated steps may include validation of file information against DICOM standards, listed and known CT manufacturers, and other standards. Validated data may be stored in the database 102, while invalid data may be flagged or generate an error result. Multiple CT series or stacks in the DICOM study may be segregated. For example, the ingestion pipeline module 126 may perform one or more analysis threshold determinations on identified medical scan images, medical data entries, etc., such as determining whether data is valid for processing, determining whether adequate data is available to perform processing, etc.

In various implementations, selection of optimal CT series may be performed via multifactorial analysis of technical characteristics of a study, e.g., as assessed by data parsed and stored via the ingestion pipeline module 124. This selection process may be built and validated using, e.g., more than five-thousand cases from over thirty healthcare institutions around the world.

Figure 9:
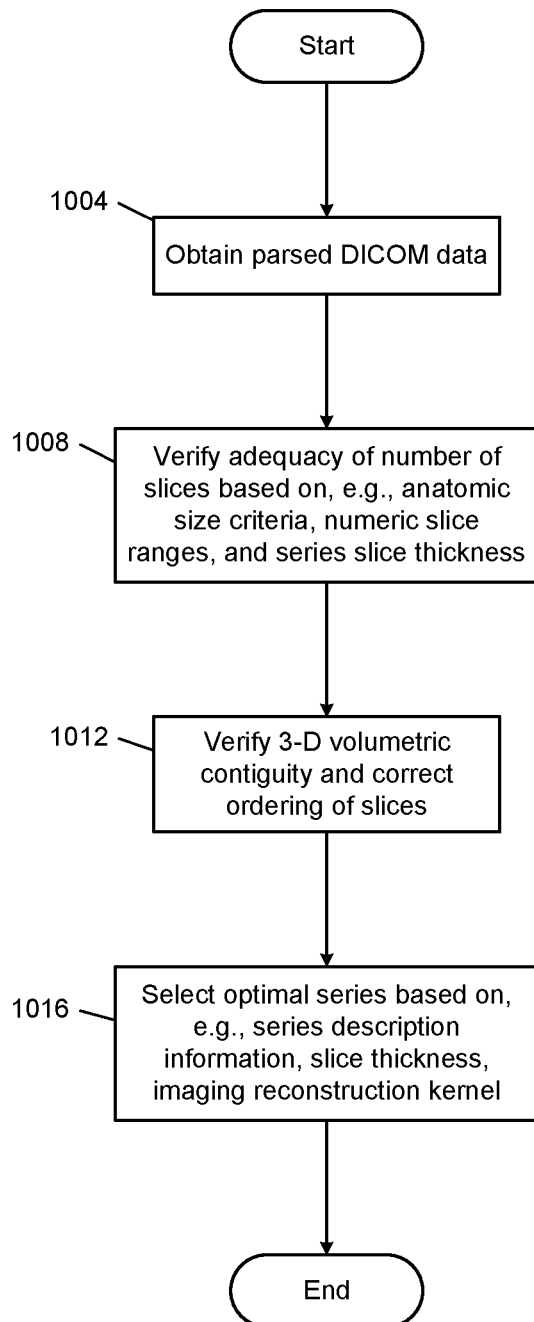
FIG. 9 is a flowchart illustrating an example process for performing selection checks on ingested data.

An example process for performing selection checks is illustrated in FIG. 9, which may be performed by, for example, the ingestion pipeline module 124. At 1004, control begins by obtaining parsed DICOM data (e.g., as parsed by the ingestion pipeline module 124 according to the case processing data 120).

At 1008, control verifies adequacy of a number of slices based on, e.g., anatomic size criteria, numeric slice ranges, series slice thicknesses, etc. Control then proceeds to 1012 to verify 3D volumetric contiguity and correct ordering of slices. At 1016, control selects an optimal series based on, e.g., series description information, slice thickness, imaging reconstruction kernel, and other technical factors. For example, a series may be selected within an optimal slice thickness range (e.g., a slice thickness that is below a specified slice thickness upper boundary and above a specified slice thickness lower boundary), a series may be selected to ensure that images are contiguous (e.g., without skipping over large sections of the body), a series may be selected based on an optimal reconstruction kernel (e.g., avoiding a kernel that optimizes for a liver when the desired target is a lung), etc.

In various implementations, the ingestion pipeline module 124 may normalize a selected series in a 3D volumetric format using padding, cropping, image fusion, etc. Imaging pixel information may be converted into a mathematical representation for processing by the analysis system module 126. The ingestion pipeline module 124 may recombine parsed text, numeric and imaging pixel information into storage for direct access of the processed data.

In some cases, the system may include flags, warnings, breakers, etc. for cases where data cannot be processed adequately, or optimized data selection is unsuccessful. In these cases, appropriate messaging may be provided to a human operator for evaluation and correction or manual re-processing. Similar modules may be available for DICOM magnetic resonance imaging (Mill) and other standard-format medical data types, using similar procedural, automated steps.

Figure 10:
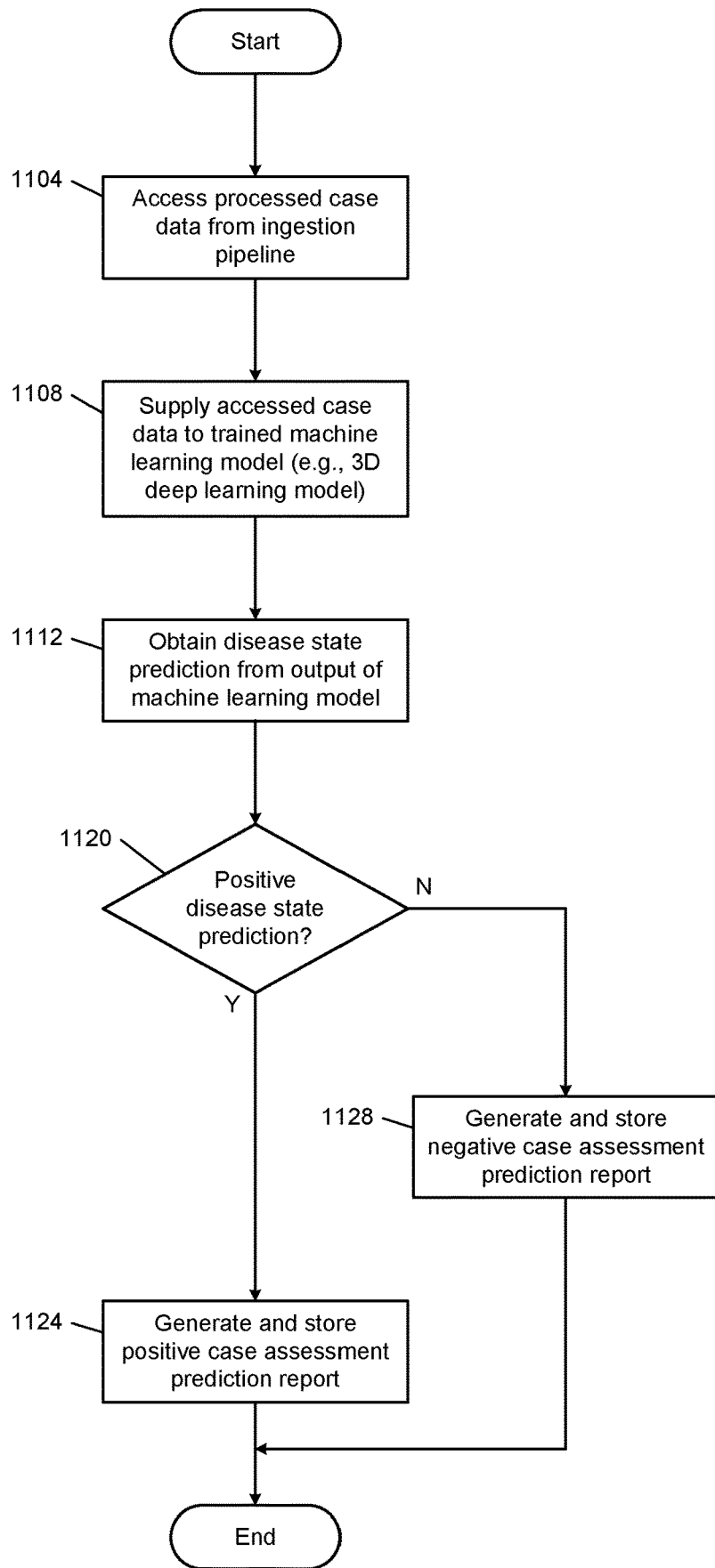
FIG. 10 is a flowchart illustrating an example process for performing a disease state prediction using a machine learning model.

FIG. 10 illustrates an example process for generating disease diagnosis predictions using, e.g., the analysis system module 126 and the machine learning model module 128. Control begins at 1104 by accessing processed case data from the ingestion pipeline module 124.

At 1108, control supplies the accessed case data to a trained machine learning model, such as a 3D deep learning model. Control then obtains a disease state prediction from an output of the machine learning model (e.g., using the machine learning model module 128), at 1112.

At 1120, control determines whether a positive disease state prediction is output by the model. If so, control proceeds to 1128 to generate and store a negative case assessment prediction report. If control determines at 1120 that a positive disease state has been predicted by the machine learning model, control proceeds to 1124 to generate and store a positive case assessment prediction report.

Conclusion

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. In the written description and claims, one or more steps within a method may be executed in a different order (or concurrently) without altering the principles of the present disclosure. Similarly, one or more instructions stored in a non-transitory computer-readable medium may be executed in different order (or concurrently) without altering the principles of the present disclosure. Unless indicated otherwise, numbering or other labeling of instructions or method steps is done for convenient reference, not to indicate a fixed order.

Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements.

The phrase "at least one of A, B, and C" should be construed to mean a logical (A OR B OR C), using a non-exclusive logical OR, and should not be construed to mean "at least one of A, at least one of B, and at least one of C." The term "set" does not necessarily exclude the empty set. The term "non-empty set" may be used to indicate exclusion of the empty set. The term "subset" does not necessarily require a proper subset. In other words, a first subset of a first set may be coextensive with (equal to) the first set.

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module. For example, the client module may include a native or web application executing on a client device and in network communication with the server module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. Such apparatuses and methods may be described as computerized apparatuses and computerized methods. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A computer system comprising:
memory hardware configured to store a three-dimensional deep learning model, a pathology outcome database including multiple computed tomography (CT) images each associated with a surgical pathology outcome value, and computer-executable instructions, wherein each surgical pathology outcome value is indicative of whether a patient experienced a disease diagnosis corresponding to a target medical condition; and
processor hardware configured to execute the instructions, wherein the instructions include:
for each of the multiple CT images:
  obtaining the surgical pathology outcome value associated with the CT image;
  in response to the surgical pathology outcome value indicating the patient experienced the disease diagnosis corresponding to the target medical condition, assigning the CT image to a positive image training dataset;
  in response to the surgical pathology outcome value indicating the patient did not experience the disease diagnosis corresponding to the target medical condition, assigning the CT image to a negative image training dataset;
  segregating data of CT image into multiple CT series or stacks;
  selecting an optimal CT series via multifactorial analysis; and
  normalizing the selected optimal CT series into a three-dimensional volumetric format in the positive image training dataset or the negative image training dataset;
supplying the positive training image dataset and the negative image training dataset to the three-dimensional deep learning model to train the three-dimensional deep learning model to generate a target medical condition prediction output, wherein the target medical condition prediction output is indicative of a likelihood that a patient will experience a future disease diagnosis corresponding to the target medical condition; and
subsequent to training the three-dimensional deep learning model, supplying a new CT image corresponding to a new patient to the three-dimensional deep learning model to generate a prediction output associated with the new CT image, and treating the new patient for a target medical condition according to the prediction output associated with the new CT image.

2. The system of claim 1, wherein:
the instructions further include, for each of the multiple CT images, obtaining at least one clinical factor parameter associated with the CT image; and
assigning the CT image to the positive image training dataset or the negative image training dataset is based on both the surgical pathology outcome value and the at least one clinical factor parameter.

3. The system of claim 2, wherein the at least one clinical factor parameter includes a pulmonary function test output.

4. The system of claim 1, wherein the surgical pathology outcome value includes at least one of a surgical biopsy result and a tissue assessment result.

5. The system of claim 1, wherein the instructions include optimizing the three-dimensional deep learning model to extract image pattern information from each of the multiple CT images.

6. The system of claim 5, wherein optimizing the three-dimensional deep learning model includes implementing a loss function which includes weighted focal loss.

7. The system of claim 5, wherein optimizing the three-dimensional deep learning model includes using a stochastic gradient descent algorithm with momentum.

8. The system of claim 1, wherein the target medical condition includes interstitial lung disease (ILD).

9. The system of claim 8, wherein the target medical condition includes idiopathic pulmonary fibrosis (IPF).

10. The system of claim 1, wherein the instructions include calibrating the three-dimensional deep learning model via scaling methods to optimize probability correlates with result outputs of the three-dimensional deep learning model.

11. The system of claim 1, wherein the three-dimensional deep learning model includes a convolutional neural network (CNN).

12. The system of claim 1, wherein the instructions include pre-training the three-dimensional deep learning model with a video-based three-dimensional general pre-training dataset.

13. The system of claim 1, wherein the positive training image dataset and the negative image training dataset each include one or more of a demographic data input, a lab result data input, a clinical questionnaire data input, and a multi-disciplinary clinical assessment data input.

14. The system of claim 1, wherein the instructions further include determining an output threshold for the three-dimensional deep learning model.

15. The system of claim 1, wherein the positive training image dataset and the negative training image dataset do not include any CT images having human-assigned labels.

16. The system of claim 1, wherein the instructions do not include performing segmentation of the CT images prior to training the three-dimensional deep learning model.

17. The system of claim 1, wherein each of the multiple CT images includes a three-dimensional full stack of CT images including multiple layered slice images.

18. A method of automated diagnosis of disease database entities, the method comprising:
accessing multiple computed tomography (CT) images each associated with a surgical pathology outcome value, wherein each surgical pathology outcome value is indicative of whether a patient experienced a disease diagnosis corresponding to a target medical condition;
for each of the multiple CT images:
  obtaining the surgical pathology outcome value associated with the CT image;
  in response to the surgical pathology outcome value indicating the patient experienced the disease diagnosis corresponding to the target medical condition, assigning the CT image to a positive image training dataset; and
  in response to the surgical pathology outcome value indicating the patient did not experience the disease diagnosis corresponding to the target medical condition, assigning the CT image to a negative image training dataset;

segregating data of CT image into multiple CT series or stacks;

selecting an optimal CT series via multifactorial analysis; and normalizing the selected optimal CT series into a three-dimensional volumetric format in the positive image training dataset or the negative image training dataset;

supplying the positive training image dataset and the negative image training dataset to a machine learning model to train the machine learning model to generate a target medical condition prediction output, wherein the target medical condition prediction output is indicative of a likelihood that a patient will experience a future disease diagnosis corresponding to the target medical condition; and subsequent to training the machine learning model, supplying a new CT image corresponding to a new patient to the machine learning model to generate a prediction output associated with the new CT image, and treating the new patient for a target medical condition according to the prediction output associated with the new CT image.

19. The method of claim 18, further comprising, for each of the multiple CT images, obtaining at least one clinical factor parameter associated with the CT image, wherein assigning the CT image to the positive image training dataset or the negative image training dataset is based on both the surgical pathology outcome value and the at least one clinical factor parameter.

20. The method of claim 18, wherein the surgical pathology outcome value includes at least one of a surgical biopsy result and a tissue assessment result.

* * * * *